US009939370B2

(12) United States Patent
Diem et al.

(10) Patent No.: US 9,939,370 B2
(45) Date of Patent: Apr. 10, 2018

(54) PHASE CORRECTION TO COMPENSATE FOR REFLECTIVE DISTORTIONS OF OPTICAL SPECTRA

(75) Inventors: Max Diem, Boston, MA (US); Benjamin Bird, Roslindale, MA (US); Milos Miljkovic, Jamaica Plain, MA (US)

(73) Assignee: Northeastern University, Boston, MA (US)

( * ) Notice: Subject to any disclaimer, the term of this patent is extended or adjusted under 35 U.S.C. 154(b) by 814 days.

(21) Appl. No.: 14/128,099

(22) PCT Filed: Jun. 25, 2012

(86) PCT No.: PCT/US2012/044054
§ 371 (c)(1),
(2), (4) Date: Aug. 4, 2014

(87) PCT Pub. No.: WO2013/039587
PCT Pub. Date: Mar. 21, 2013

(65) Prior Publication Data
US 2015/0019155 A1    Jan. 15, 2015

Related U.S. Application Data

(60) Provisional application No. 61/500,999, filed on Jun. 24, 2011.

(51) Int. Cl.
*G01N 21/31*    (2006.01)
*G01N 21/35*    (2014.01)
(Continued)

(52) U.S. Cl.
CPC ............. *G01N 21/255* (2013.01); *G01J 3/28* (2013.01); *G01N 21/1702* (2013.01);
(Continued)

(58) Field of Classification Search
CPC ........ G01N 21/31; G01N 21/35; G01N 21/65; G01N 21/255; G01N 21/1702;
(Continued)

(56) References Cited

U.S. PATENT DOCUMENTS 4,927,296 A   5/1990  Kaldenbach
5,450,196 A   9/1995  Turner
(Continued)

FOREIGN PATENT DOCUMENTS

JP   2006-003191 A   1/2006
JP   2007-083759 A   4/2007
(Continued)

OTHER PUBLICATIONS

Bassan, et al., "Reflection Contributions to the Dispersion Artefact in FTIR Spectra of Single Biological Cells," Analyst, vol. 134, pp. 1171-1175 (2009).
(Continued)

*Primary Examiner* — Bryan Bui
(74) *Attorney, Agent, or Firm* — Foley Hoag LLP; Rajesh Vallabh

(57) ABSTRACT

Disclosed herein is a process and system to correct reflective distortions of an optical spectrum. In addition, a spectroscopy system that compensates for reflective distortions is disclosed.

36 Claims, 12 Drawing Sheets

(51) Int. Cl.
*G01J 3/28* (2006.01)
*G01N 21/25* (2006.01)
*G01N 21/65* (2006.01)
*G01N 21/17* (2006.01)
*G01N 21/3563* (2014.01)

(52) U.S. Cl.
CPC ............ *G01N 21/31* (2013.01); *G01N 21/35* (2013.01); *G01N 21/65* (2013.01); *G01N 21/3563* (2013.01); *G01N 2201/10* (2013.01); *G01N 2201/121* (2013.01)

(58) Field of Classification Search
CPC ........... G01N 21/3565; G01N 2201/10; G01N 2201/121; G01J 3/28
USPC ....................................................... 702/104
See application file for complete search history.

(56) References Cited

U.S. PATENT DOCUMENTS

| | | | |
|---|---|---|---|
| 6,208,752 | B1 | 3/2001 | Palmadesso et al. |
| 2004/0153300 | A1 | 8/2004 | Symosek et al. |
| 2004/0239946 | A1 | 12/2004 | Kane et al. |
| 2005/0288027 | A1 | 12/2005 | Cho et al. |
| 2007/0152154 | A1 | 7/2007 | DeCamp et al. |
| 2008/0170219 | A1 | 7/2008 | Sarunic et al. |
| 2008/0198374 | A1 | 8/2008 | Desbiens et al. |
| 2008/0228844 | A1 | 9/2008 | Bohlen et al. |
| 2011/0096333 | A1 | 4/2011 | Suehira et al. |
| 2012/0082362 | A1* | 4/2012 | Diem .................. A61B 5/0071 382/133 |
| 2013/0222801 | A1* | 8/2013 | Harel ........................ G01J 3/10 356/328 |

FOREIGN PATENT DOCUMENTS

| | | | |
|---|---|---|---|
| JP | 2007-529721 | A | 10/2007 |
| JP | 2008-502915 | A | 1/2008 |
| JP | 2009-530614 | A | 8/2009 |
| JP | 2011-087814 | A | 5/2011 |
| WO | WO-2011/163624 | A1 | 12/2011 |

OTHER PUBLICATIONS

Bassan, et al., "Resonant Mie Scattering (RMieS) Correction of Infrared Spectra from Highly Scattering Biological Samples," Analyst, vol. 135, pp. 268-277 (2010).

Bassan, et al., "Resonant Mie Scattering in Infrared Spectroscopy of Biological Materials—Understanding the 'Dispersion Artefact'," Analyst, vol. 134, pp. 1586-1593 (2009).

Bird, et al., "Cytology by Infrared Micro-Spectroscopy: Automatic Distinction of Cell Types in Urinary Cytology," Vibr.Spectrosc., vol. 48(1), pp. 101-106 (2008).

Bird, et al., "Detection of Breast Micro-metastases in Axillary Lymph Nodes by Infrared Micro-spectral Imaging," The Analyst, vol. 134, pp. 1067-1076 (2009).

Bird, et al., "Spectral Detection of Micro-Metastases and Individual Metastatic Cells in Lymph Node Histology," Tech.Cancer Res. Treatment, vol. 10, pp. 135-144 (2011).

Bird, et al., "Two Step Resonant Mie Scattering Correction of Infrared Micro-spectral Data: Human Lymph Node Tissue," J. Biophoton., vol. 3 (No. 8-9), pp. 597-608 (2010).

Diem, et al., "Infrared Spectroscopy of Human Cells and Tissue. VIII. Strategies for Analysis of Infrared Tissue Mapping Data and Applications to Liver Tissue," Biopolymers, vol. 57, pp. 282-290 (2000).

International Search Report and Written Opinion issued by the U.S. Patent and Trademark Office as International Searching Authority for International Application No. PCT/US12/44054 dated Mar. 25, 2013 (12 pgs.).

Kohler, et al., "Estimating and Correcting Mie Scattering in Synchrotron-Based Microscopic Fourier Transform Infrared Spectra by Extended Multiplicative Signal Correction," Appl.Spectrosc., vol. 62, pp. 259-266 (2008).

Kohler, et al., "Extended Multiplicative Signal Correction as a Tool for Separation and Characterization of Physical and Chemical Information in Fourier Transform Infrared Microscopy Images of Cryo-sections of Beef Loin," Appl. Spectrosc., vol. 59, pp. 707-716 (2005).

Lasch, et al., "Artificial Neural Networks as Supervised Techniques for FT-IR Microspectroscopic Imaging," J. Chemometrics, vol. 20, pp. 209-220 (2007).

Mohlenhoff, et al., "Mie-Type Scattering and Non-Beer-Lambert Absorption Behavior of Human Cells in Infrared Microspectroscopy," Biophys J, vol. 88, pp. 3635-3640 (2005).

Papamarkakis, et al., "Cytopathology by Optical Methods: Spectral Cytopathology of the Oral Mucosa," Laboratory Investigations, vol. 90, pp. 589-598 (2010).

Romeo, et al. "Vibrational Microspectroscopy of Cells and Tissues," Biomedical Vibrational Spectroscopy, pp. 121-152 (2008).

Romeo, et al., "Infrared micro-spectroscopic studies of epithelial cells," Biochim Biophys Acta, vol. 1758, pp. 915-922 (Jul. 2006).

Romeo, et al., "Infrared Micro-spectroscopy of Human Cells: Causes for the Spectral Variance of Oral Mucosa (Buccal) Cells," Vibrational Spectrosc., vol. 42, pp. 9-14 (2006).

Romeo, et al., "Infrared Spectral Imaging of Lymph Nodes: Strategies for Analysis and Artifact Reduction," Vibrational Spectrosc., vol. 38, pp. 115-119 (2005).

Romeo, M. and Diem, M.J., "Correction of dispersive Line Shape Artifact Observed in Diffuse Reflection Infrared Spectroscopy and Absorption/Reflection (Transflection) Infrared Micro-spectroscopy," Vibrational Spectroscopy, vol. 38, pp. 129-132 (2005).

Schubert, et al., "Spectral Cytopathology of Cervical Samples: Detecting Cellular Abnormalities in Cytologically Normal Cells," Laboratory Investigations, vol. 90, pp. 1068-1077 (2010).

Wong, et al., "Infrared Spectroscopy of Exfoliated Human Cervical Cells: Evidence of Extensive Structural Changes During Carcinogenesis," Proc. Natl. Acad. Sci., vol. 88, pp. 10988-10992 (Dec. 1991).

Notice of Allowance in Japanese Patent Application JP 2014-517253 dated Feb. 14, 2017.

Office Action in Japanese Patent Application JP 2014-517253 dated Apr. 4, 2016.

* cited by examiner

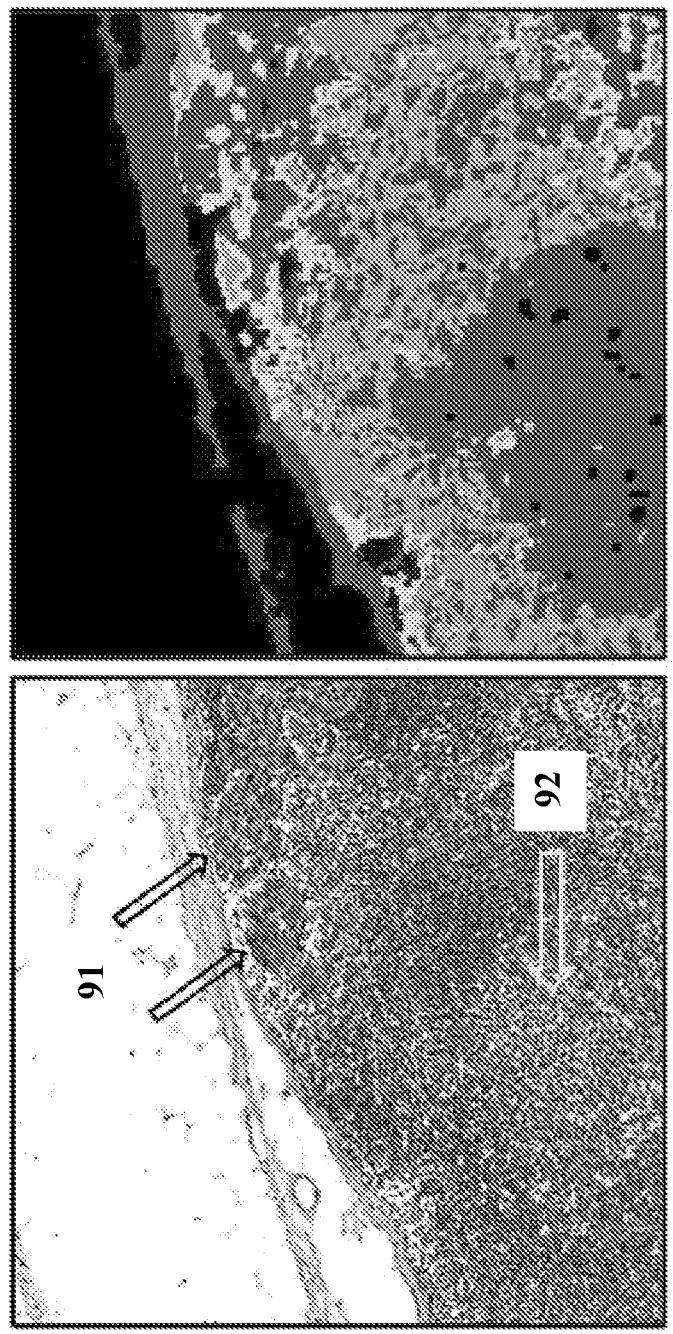

PHASE CORRECTION TO COMPENSATE FOR REFLECTIVE DISTORTIONS OF OPTICAL SPECTRA

This application is a U.S. National Stage Application under 35 U.S.C. § 371 of International Application No. PCT/US12/044054, filed Jun. 25, 2012, which claims the benefit of priority under 35 U.S.C. 119(e) from U.S. Provisional Application No. 61/500,999, filed Jun. 24, 2011, the contents of which are hereby incorporated by reference in their entirety.

STATEMENT REGARDING FEDERALLY SPONSORED RESEARCH/DEVELOPMENT

This research was funded by grants from the National Institutes of Health (under CA 090346) and a Department of Homeland Security Center of Excellence grant (2008-ST-061-ED001).

FIELD OF THE INVENTION

The invention is generally directed to physical and analytical chemistry with applications in other fields such as quantum mechanics and remote sensing. More specifically, the invention is directed to technologies useful for improving visualization of samples by methods of vibrational spectroscopy and vibrational micro-spectroscopy.

BACKGROUND OF THE INVENTION

Novel methods of medical diagnostics based on vibrational spectroscopy and vibrational micro-spectroscopy (e.g., infrared and Raman) capture a spectral snapshot of the averaged biochemical composition of cells and tissues rather than relying on subjective and inefficient studies of cell morphology and tissue architectural features. For example, infrared micro-spectroscopy is now applied to the study of cell diseases ("Spectral Cytopathology" or "SCP") and the study of tissue diseases ("Spectral Histopathology" or "SHP"). However, in both SCP and SHP, as well as other spectroscopy applications, researchers have observed the contamination of spectral patterns by certain artifacts that aggravate spectral analysis by causing a contaminated spectrum to be classified differently (in terms of chemical content) than it would be if uncontaminated.

Until recently, the source of the contamination was not completely understood, and it was considered that the contamination was due to chemical variations within the sample or instrument software malfunction.

More recently, the contamination has been attributed to the superimposition of reflective band shapes on absorbance band shapes due to Mie scattering by spherical particles, such as cellular nuclei or spherical cells, and the anomalous dispersion of the refractive index. The interaction of Mie scattering and the mixing of dispersive band shapes are known as Resonance Mie ("RMie") scattering.

Mie scattering manifests as broad, undulating background features as can be seen in FIG. 3. Meanwhile, the RMie scattering artifacts are visible in FIG. 2. The bottom trace 21 represents an uncontaminated spectral band shape for biological tissue. Meanwhile, the top trace 22 depicts a spectral band shape strongly contaminated by reflective components, namely an intensity shift 23 and a frequency shift 24. The differences between the two traces in FIG. 2 indicate that the spectral distortions are independent of the chemical composition but depend, instead, on the morphology of the sample.

In addition to distorting SCP and SHP optical spectra, RMie scattering artifacts frequently occur with applications using Diffuse Reflectance Infrared Fourier Transform Spectroscopy ("DRIFTS"), Attenuated Total Reflectance ("ATR") spectroscopy, Coherent Anti-Stokes Raman Spectroscopy ("CARS"), and other forms of spectroscopy in which the real and imaginary parts of the complex refractive index mix significantly. Thus, distorted band shapes result not only from the interaction between reflectance and absorbance but from anomalous dispersion of the refractive index relating to other physical parameters, such as the resonant and non-resonant signal components at play in CARS.

There have been ongoing attempts to compensate for distorted band shapes as arising from the superposition of reflective components onto the absorbance features of infrared spectra. In one approach, researchers attributed these effects to incorrect phase correction of the instrument control software. Other researchers have applied existing methods for removing Mie scattering distortions. For example, the Extended Multiplicative Signal Correction ("EMSC") method iteratively corrected each spectrum of a dataset according to a "reference" spectrum, initially the mean spectrum of the dataset or an "artificial" spectrum (e.g., the spectrum of a pure protein matrix). In one iteration, a dataset of 1000 spectra produced 1000 corrected spectra. Then, each corrected spectrum was used as the reference for the subsequent iteration, thus requiring 1,000,000 correction runs. At about ten passes and computation times measured in days, a stable level of corrected output spectra was highly inefficient.

More recently, researchers have eliminated scattering and reflective band shapes from spectra by obtaining the reflective components (the "interference spectra") via the Kramers-Kronig transform and the Mie scattering curves via the van Hulst equation. Then, the distorting components were subtracted from all the spectra in a dataset via EMSC. This process avoided the slow, iterative approach by carrying out a preliminary cluster analysis of the dataset and selecting the spectrum with the highest amide I frequencies in each cluster as the "uncontaminated" reference spectrum. This process also accounted for multiple interference spectra; however, the definition of such interference spectra added subjectivity to the process.

BRIEF SUMMARY OF THE INVENTION

Embodiments disclosed herein provide a spectroscopy system and process to compensate for reflective distortions of optical spectra. Briefly described, one embodiment of the system, among others, can be implemented as follows. The system may comprise an energy emission device; a detection device; a memory; and a processor configured through the memory to perform the steps of correcting reflective distortions of an optical spectrum. In another embodiment, the system compensates for optical spectra where the distorted line shapes are not caused by the interaction of reflectance and absorbance, but other physical parameters, such as resonant and non-resonant signal components, such as in CARS. This system may comprise an energy emission device; a detection device; a processor; and a memory in electronic communication with the processor; wherein the memory stores computer executable code that when executed by the processor performs the steps of correcting distortions caused by resonant and non-resonant signal components.

For biological applications, in spectral datasets consisting of many tissue types, the extraction of uncontaminated spectra (from which the "interference spectra" are derived) can become tedious. Under these conditions, it is unclear whether or not the fitting of all spectra in the dataset to the most appropriate interference spectrum is guaranteed. Thus, a method based on a revised phase correction approach, in which no input data are required and that is computationally fast is presented. It takes into account mitigating factors such as Mie and RMie scattering and other distortive effects based on the anomalous dispersion of the refractive index.

The approach disclosed here first transforms all spectra into the optical path-difference domain by reverse Fourier transform. For each spectrum, this process yields both a real and an imaginary interferogram. After zero-filling each interferogram by a factor of two, the padded interferograms are forward-Fourier transformed to yield an imaginary spectral part, which consists of the purely absorptive portion of the spectrum and exhibits absorptive band shapes, and a real spectral part, which exhibits the same dispersive band shapes obtained via numeric Kramers-Kronig transform. By recombining the real and imaginary parts with the optimal phase angle between them, an artifact-free spectrum is obtained.

Additionally, since the phase required to correct the contaminated spectra cannot be determined experimentally, and varies from spectrum to spectrum, phase angles are determined using a stepwise approach between −90 and 90 degrees, in user selectable steps. The "best" spectrum is determined by analysis of peak position and intensity criteria, both of which vary during phase correction. Such a spectrum is the endpoint at which the computation ends. The broad undulating Mie scattering contributions are not corrected for explicitly in this approach, but they disappear by performing the phase correction computation on second derivative spectra, which exhibit a scatter-free background.

Certain aspects can also be viewed as providing a process for correcting reflective distortions of an optical spectrum. In one embodiment, the process includes: scanning a sample with an infrared or other energy waveform emission to obtain at least one spectrum; pre-processing the at least one spectrum; performing reverse Fourier transformation to obtain a real interferogram and an imaginary interferogram from the at least one spectrum; zero-filling the interferograms; performing forward Fourier transformation to obtain a real part and an imaginary part of the at least one spectrum; and recombining the real part and the imaginary part using trial phase angles to obtain at least one phase-corrected spectrum, the at least one phase-corrected spectrum being substantially free of dispersive band shapes.

The present system and process have at least the following interrelated advantages over previous approaches: computational speed (5000 spectra/second), no requirement for a priori input data on the hyperspectral dataset, easy incorporation of the process into spectral imaging and digital staining diagnostic routines (e.g., for automatic cancer detection and diagnosis in SCP and SHP), applicability to other forms of spectroscopy in which band shapes are distorted by reflective artifacts (e.g., DRIFTS, ATR spectroscopy, and CARS), and a basis in the properly understood, underlying physical principles.

Other systems, processes, and features will become apparent to one with skill in the art upon examination of the following drawings and detailed description. It is intended that all such additional systems, processes, and features be included within this description, be within the scope of the present invention, and be protected by the accompanying claims.

DESCRIPTION OF THE FIGURES

The following figures are presented for the purpose of illustration only, and are not intended to be limiting:

FIG. 9 is a photomicrograph depicting a human lymph node tissue section;

FIG. 10 is an image depicting a human lymph node tissue section obtained via hierarchical cluster analysis of a hyperspectral dataset contaminated by RMie scattering artifacts;

DETAILED DESCRIPTION OF THE INVENTION

Figure 1:
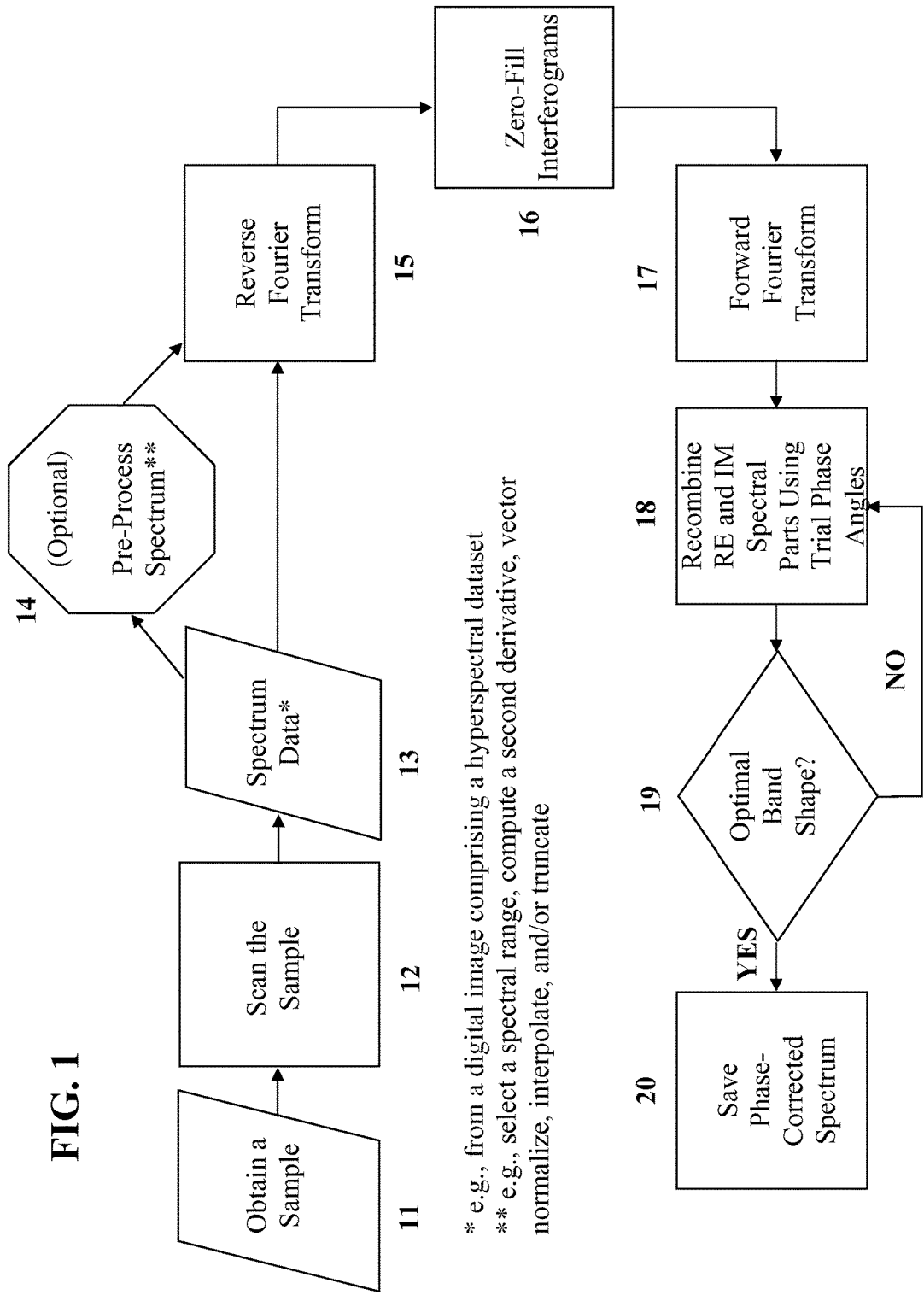
FIG. 1 is a flow diagram in accordance with some embodiments.

All publications, patent applications, patents, and other references mentioned herein are incorporated by reference in their entirety. In case of conflict, the present specification, including definitions, will control. In addition, the materials, methods, and examples are illustrative only and not intended to be limiting.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Definitions

For convenience, certain terms employed in the specification, example, and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

In general, the compositions of the disclosure can be alternately formulated to comprise, consist of, or consist essentially of, any appropriate components disclosed in this disclosure. The compositions of the disclosure can additionally, or alternatively, be formulated so as to be devoid, or substantially free, of any components, materials, ingredients, adjuvants, or species used in the prior art compositions or that are otherwise not necessary to the achievement of the function and/or objectives of the present disclosure.

The articles "a" and "an" are used in this disclosure to refer to one or more than one (i.e., to at least one) of the grammatical object of the article. By way of example, "an element" means one element or more than one element.

The term "or" is used in this disclosure to mean, and is used interchangeably with, the term "and/or," unless indicated otherwise.

The term "spectrum" is used in this disclosure to mean data representing signal intensity or power as a function of frequency. The concept of frequency has the same relationships to the concepts of wavelength and wavenumber as is commonly understood by one of ordinary skill in the art to which this disclosure belongs.

The term "hyperspectral dataset" is used in this disclosure to mean a construct consisting of $N=n \cdot m$ individual spectra or spectral vectors (representing, e.g., absorbance, reflectance, or emission), each consisting of k intensity data points, which are usually spaced equally in the frequency domain (i.e., signal intensity versus frequency). Each spectrum is associated with a distinct pixel of the sample, and can be located by its coordinates x and y, with $1 \leq x \leq n$, and $1 \leq y \leq m$.

The term "phase difference" is used in this disclosure to mean a difference between two waveforms of the same frequency and referenced to the same point in time. Phase difference may be expressed in time units, degrees from 0° to 360°, or radians from 0 to $2\pi$. Thus, the term "phase angle" is used in this disclosure to mean an angular difference between two waveforms of the same frequency and referenced to the same point in time.

The term "band" or "band shape" or "band profile" is used in this disclosure to mean a range of frequencies, which are able to excite particular transitions in a substance (e.g., absorbance, reflectance, or emission), or a plot of spectrum signal intensity as a function of the frequencies. Absorbance band shapes correspond to the imaginary part k of the complex refractive index:

$$\tilde{n} = n + ik$$

Reflectance band shapes correspond to the real part n of the complex refractive index, and can be obtained from absorbance bands by the numeric Kramers-Kronig transformation, or as the real part of the complex Fourier transform.

The term "second derivative spectrum" is used in this disclosure to mean a second derivation of a spectrum signal intensity with respect to frequency or wavenumber.

The term "reverse Fourier transform" is used in this disclosure to mean the conversion of a spectrum from the frequency domain (i.e., signal intensity as a function of wavenumber) to the path-difference domain (i.e., signal intensity as a function of optical path difference). The term "forward Fourier transform" is used in this disclosure to mean the conversion of a spectrum from the path-difference domain to the frequency domain.

Figure 3:
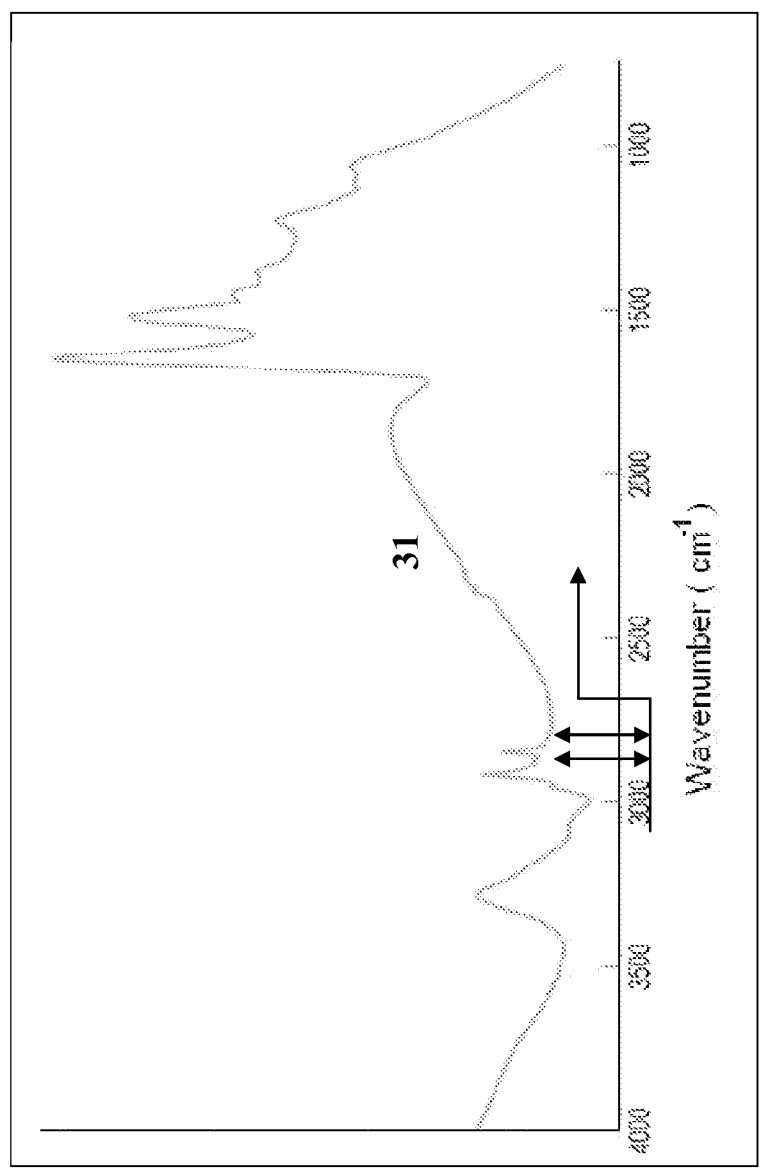
FIG. 3 is a plot depicting the spectral background features attributed to Mie scattering by spherical particles.

The term "Mie scattering" is used in this disclosure to mean a morphology-dependent distortion of the spectral band profile, which results from the use of a sample that is non-uniform and consists of particles (e.g., cellular nuclei or spherical cells) of about the same size as the wavelength of the light interrogating the sample. Mie scattering manifests as broad, undulating background features as can be seen in FIG. 3.

Figure 4:
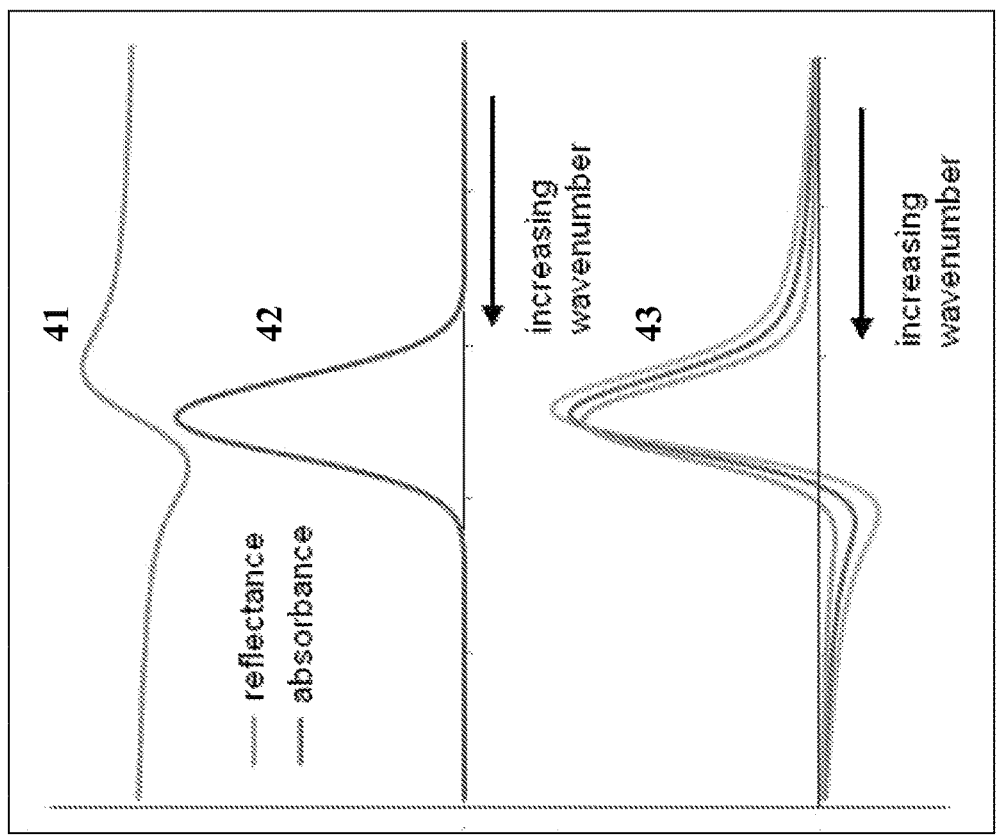
FIG. 4 is a plot depicting anomalous dispersion of the refractive index for an infrared spectrum.

The term "Resonance Mie (RMie) scattering" is used in this disclosure to mean a distortion of the spectral band profile, as modeled in FIG. 4, due to the mixing of the reflectance band shape 41 and the absorbance band shape 42. More specifically, what appears as a shift in the signal intensity and frequency of the band shape 43 results from anomalous dispersion of the refractive index. This distortion occurs whenever the sample absorptivity goes through a maximum (i.e., over the profile of an absorbance band) and is linked to Mie scattering and other optical effects that depend on the refractive index.

The term "phase-corrected spectrum" is used in this disclosure to mean a spectrum that has been corrected for Mie and RMie scattering according to an embodiment of the invention.

System and Process

The disclosure provides, in part, systems and processes to compensate for reflective distortions of an optical spectrum obtained through forms of spectroscopy in which the real and imaginary parts of the complex refractive index mix. This mixing can occur through a variety of physical processes, and is particularly pronounced when measurements are carried out in reflectance mode. In particular, the systems and processes utilize a defined endpoint for correcting reflective distortions. In some embodiments, the reflective distortions observed in a spectrum are corrected through adjustments to optimize the phase angle between the real and imaginary parts of the spectrum. Although phase correction is routinely used in the pre-processing of interferograms in certain forms of spectroscopy, where the proper phase angle can be determined experimentally (e.g., Fourier transform infrared and nuclear magnetic resonance spectroscopy), phase correction has not been applied retroactively to remedy reflective distortions for a spectrum corrupted by RMie scattering.

The present system may be used to provide spectroscopy results, including digital images that are corrected for reflective distortions. The system includes an energy emission device, a detection device, and logic directed to adjusting the phase of a spectrum contaminated by Mie or RMie scattering.

The energy emission device generates a waveform for analysis of the chemical composition of a sample. The emission device is not limited to a microwave generator, a broadband source, or a laser. In certain embodiments, the system comprises a separate disperser that divides the emitted waveform into its component wavelengths before scanning a sample.

The detection device receives the relative intensities of the component wavelengths emitted or reflected by or through a sample. The detection device is a detector, such as, but not limited to, a photoemissive detector (e.g., a photomultiplier, an imaging tube, or a microchannel plate) or a photoconductive detector (e.g., a semiconductor), arranged as a single detector or a detector array. Energy emission devices and detector devices as are well known in the art can be used.

The logic for using the results of the detection device can be implemented in software, firmware, hardware, or a combination thereof. In a first exemplary embodiment, at least a portion of the present system is implemented in software, as an executable program, and is executed by a special or general-purpose digital computer, such as a personal computer, workstation, minicomputer, or mainframe computer. Generally, in terms of hardware architecture, the computer includes a processor, memory, storage device, and one or more input or output devices that are communicatively coupled via a local interface. In an alternative embodiment, the system is implemented in hardware using technologies well-known in the art.

In one embodiment of the system, a scanning device comprising an energy emission device scans a sample. An energy emission device emits an energy emission that contacts the sample. The energy emission may be, but is not limited to, electromagnetic radiation (e.g., a photon) in the form of visible light, ultraviolet light, gamma radiation, X-radiation, and infrared light. The emission is absorbed by the sample, scattered by the sample, or transmitted through the sample. The scanning device comprises a detector that detects energy subsequently emitted or reflected by or through the sample. The scanning device comprises logic for converting the detected energy into an image and compensating for reflective distortions. Suitable scanning devices may include, but are not limited to, one or more of a spectrometer, a photometer, a spectrophotometer, a spectroscope, a spectrograph, a spectrum analyzer, a polychromator, a monochromator, a prism, a diffraction grating, an optical filter, a collimator, and/or an optical detector.

Figure 15:
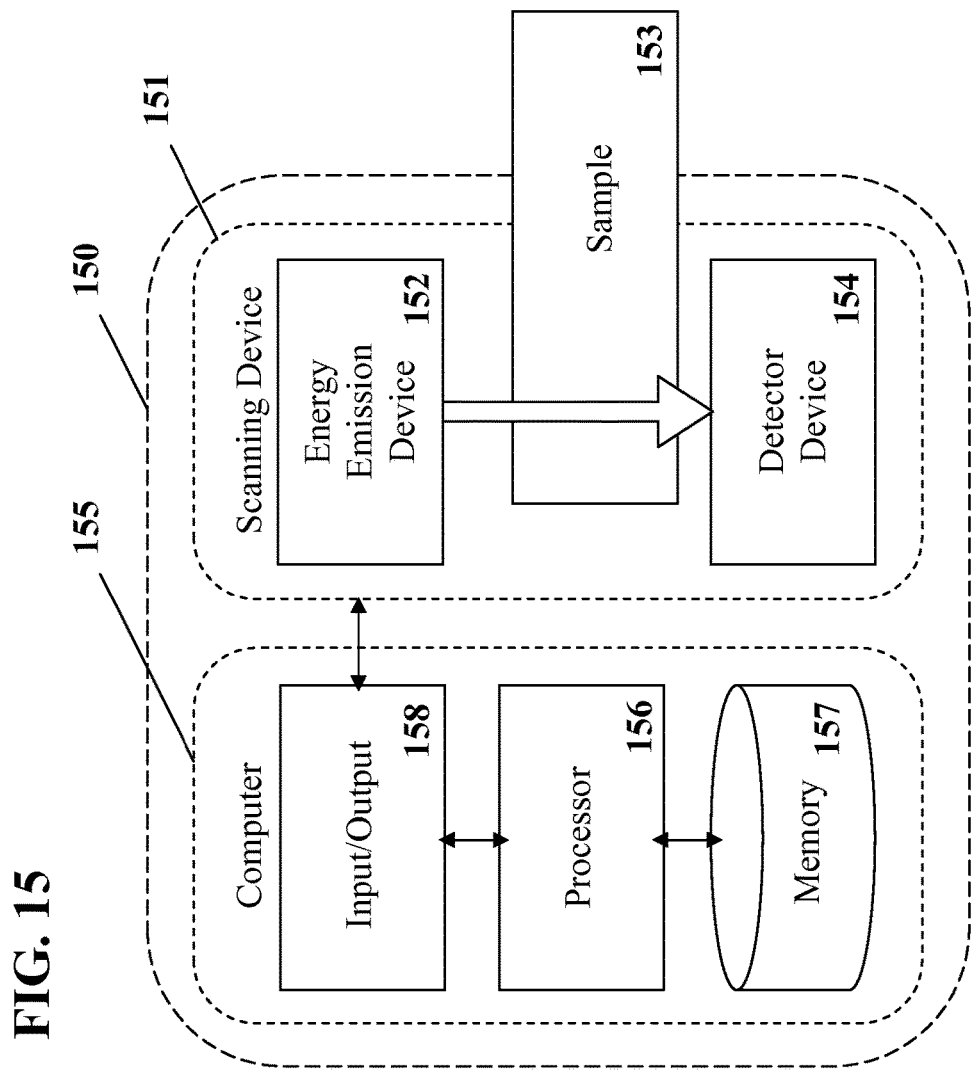
FIG. 15 is a component diagram in accordance with some embodiments.

FIG. 15 illustrates the components of the system 150 in accordance with some embodiments. A scanning device 151 comprising an energy emission device 152 generates electromagnetic waveforms for analysis of a sample 153. A detection device 154 in the scanning device receives the relative intensities of the component wavelengths emitted, transmitted, or reflected by or through the sample 153. At least a portion of the logic for using the results of the scanning device 151 is implemented in software, as an executable program, and is executed by a computer 155. The computer 155 includes a processor 156, memory 157, and one or more input or output devices 158 that are communicatively coupled via a local interface. The memory 157 is in electronic communication with the processor 156, wherein the memory 157 stores computer executable code that when executed by the processor 156 causes the processor 156 to correct distortions in the results of the scanning device 151.

Having generally described the devices in the present system, the following further describes the logic used in the present system and a process for correcting reflective distortions of a spectrum.

FIG. 1 illustrates the steps of an exemplary process for correcting reflective distortions of a spectrum. The process described may be applied to a single spectrum or each spectrum of a hyperspectral dataset or digital image 13. In step 12 of the embodiment of FIG. 1, a sample 11 is scanned with an energy emission to receive a spectrum 13.

Figure 2:
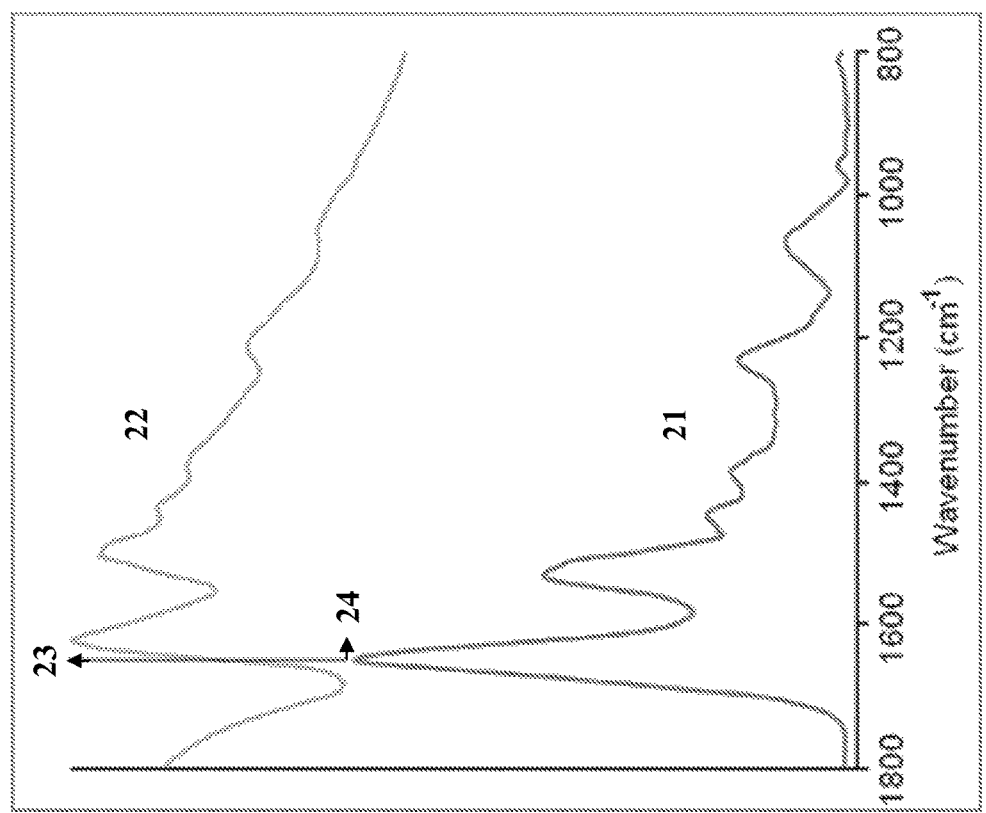
FIG. 2 is a series of plots depicting an absorbance spectrum of biological tissue both with and without reflective distortions.

Next, the spectrum 13 is pre-processed for correction (FIG. 1, step 14). In some embodiments, this step may include selecting an appropriate spectral range (e.g., a fingerprint region). A fingerprint region is a spectral range in which different compounds produce different spectral patterns. In particular applications, this region contains all the heavy atom stretching or bending vibrations or X—H deformation modes, where X is a heavy atom with an atomic number ≥12 and H is a hydrogen atom. For example, the fingerprint region of a typical infrared spectrum is usually between 800 and 1800 $cm^{-1}$ (wavenumber) (see FIG. 2).

Figure 5:
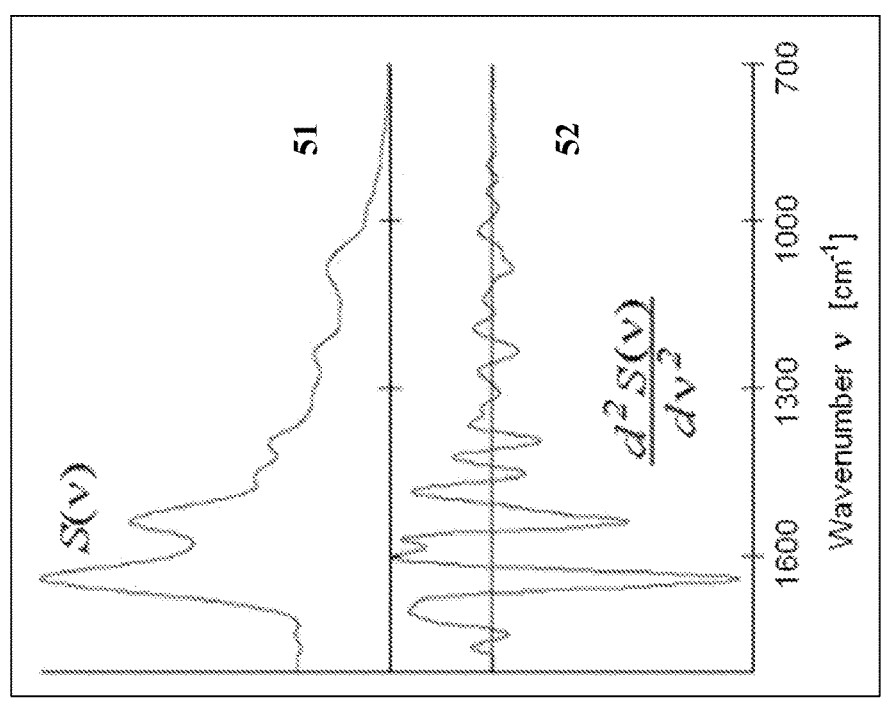
FIG. 5 is a series of plots depicting an absorbance spectrum and a second derivative of the spectrum.

In some embodiments, step 14 may include calculating a second derivative of the spectrum. FIG. 5 shows a typical spectrum 51, superimposed on a linear background, as well as a second derivative spectrum 52, obtained by taking the second derivative of the spectrum signal intensity with respect to frequency or wavenumber. Some embodiments use a Savitzky-Golay sliding window algorithm to compute a second derivative spectrum. In other embodiments, a second derivative spectrum is computed in the frequency domain (i.e., signal intensity as a function of frequency or wavenumber) by multiplying the interferogram (i.e., signal intensity as a function of optical path dependence) by an appropriately truncated quadratic function.

Figure 8:
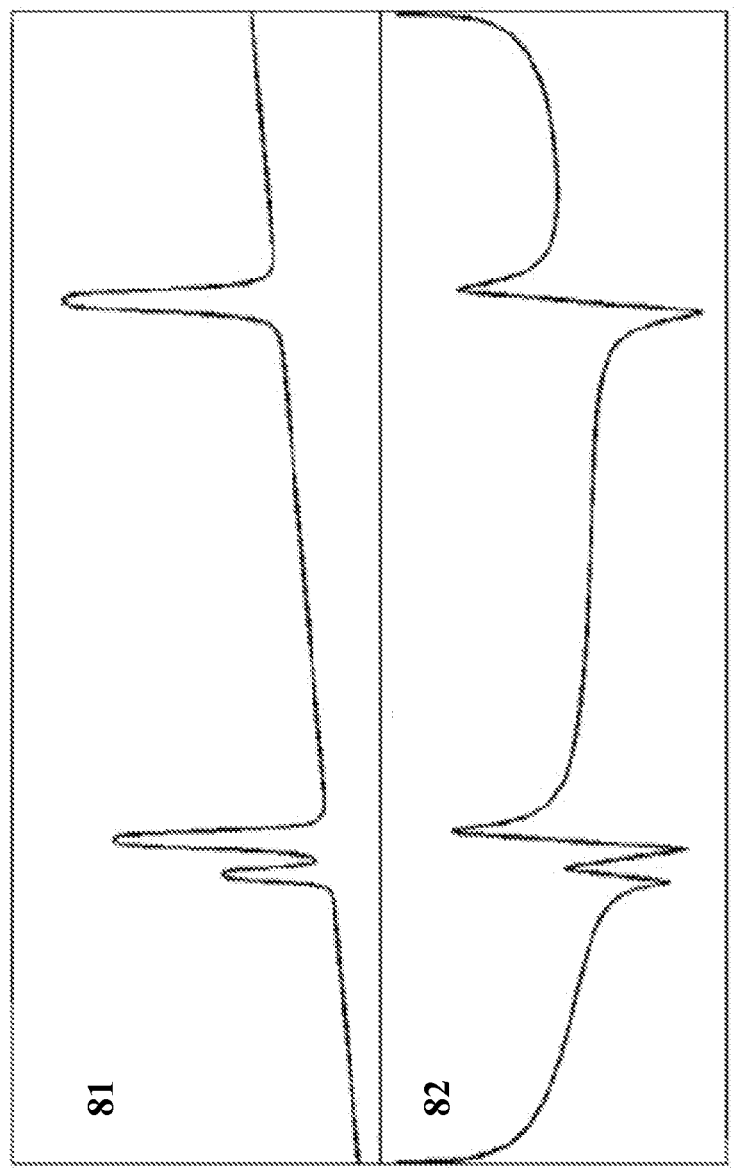
FIG. 8 is a series of plots depicting an absorbance spectrum contaminated by scattering effects and the resulting imaginary part of a forward Fourier transform of the spectrum.

Certain embodiments use a spectrum, while other embodiments use a second derivative spectrum as an input. In some embodiments, a second derivative is calculated to diminish the affects of distortions. As shown schematically in FIG. 8, if a spectrum is contaminated by Mie scattering effects that mimic a baseline slope 81, then the imaginary part of the forward Fourier transform 82 of that spectrum exhibits strongly curved effects at the spectral boundaries, which will contaminate the resulting phase-corrected spectrum. However, differentiation eliminates the sloping background features to yield a spectrum free of Mie scattering artifacts. Furthermore, common analyses of spectral data (e.g., using hierarchical cluster analysis, segmenting, or other diagnostic algorithms) are already carried out on second derivative spectra, thus minimizing future need for anti-differentiation. Therefore, it is advantageous to use a second derivative spectrum in certain embodiments.

In some embodiments, step 14 may include vector normalizing the spectrum to compensate for varying sample thickness (FIG. 1, step 14). In further embodiments, step 14 may include interpolating or truncating the spectrum to an appropriate data point length to compute a discrete Fourier transform via Fast Fourier Transform algorithm ("FFT"), which can be applied only if the vector to be transformed has a length equal to an integer power of 2. Typical data point lengths are 512, 1024, or 2048 data points (i.e., function evaluations to be used in the Fourier transform calculation).

Figure 6:
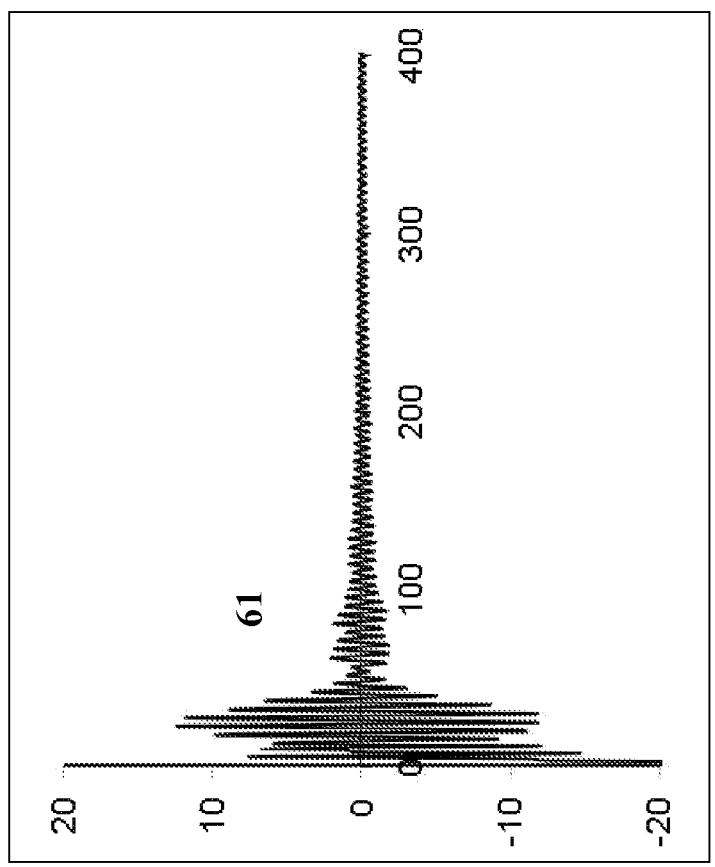
FIG. 6 is a plot depicting the real part of a forward Fourier transform of a spectrum.

In step 15 of the embodiment of FIG. 1, reverse Fourier transformation is performed on the spectrum to obtain a real interferogram and an imaginary interferogram, each of NFT/2 data points. A portion of a real interferogram is shown in FIG. 6.

To avoid erroneous signal reduction (i.e., the picket-fence effect), step 16 of the embodiment of FIG. 1 calls for adding zero-values to the end of the interferograms prior to performing forward Fourier transformation (step 17). This increase in the number of interferogram data points results in an increase in the number of sample points per frequency in the spectrum and is particularly beneficial before applying the discrete Fourier transform. A zero-filling factor of two (i.e., zero-filling until the interferogram is twice its original length) is suggested. Thus, the second NFT/2 data points of each interferogram would be zero-filled to produce two zero-filled interferograms with total lengths of NFT.

In step 17 of the embodiment of FIG. 1, forward Fourier transformation is performed on the zero-filled interferograms to obtain an imaginary part of the spectrum, exhibiting the absorbance band profile, and a real part of the spectrum, exhibiting the same reflectance band shapes that would be obtained from the absorbance band profile via the numeric Kramers-Kronig transform.

Figure 7:
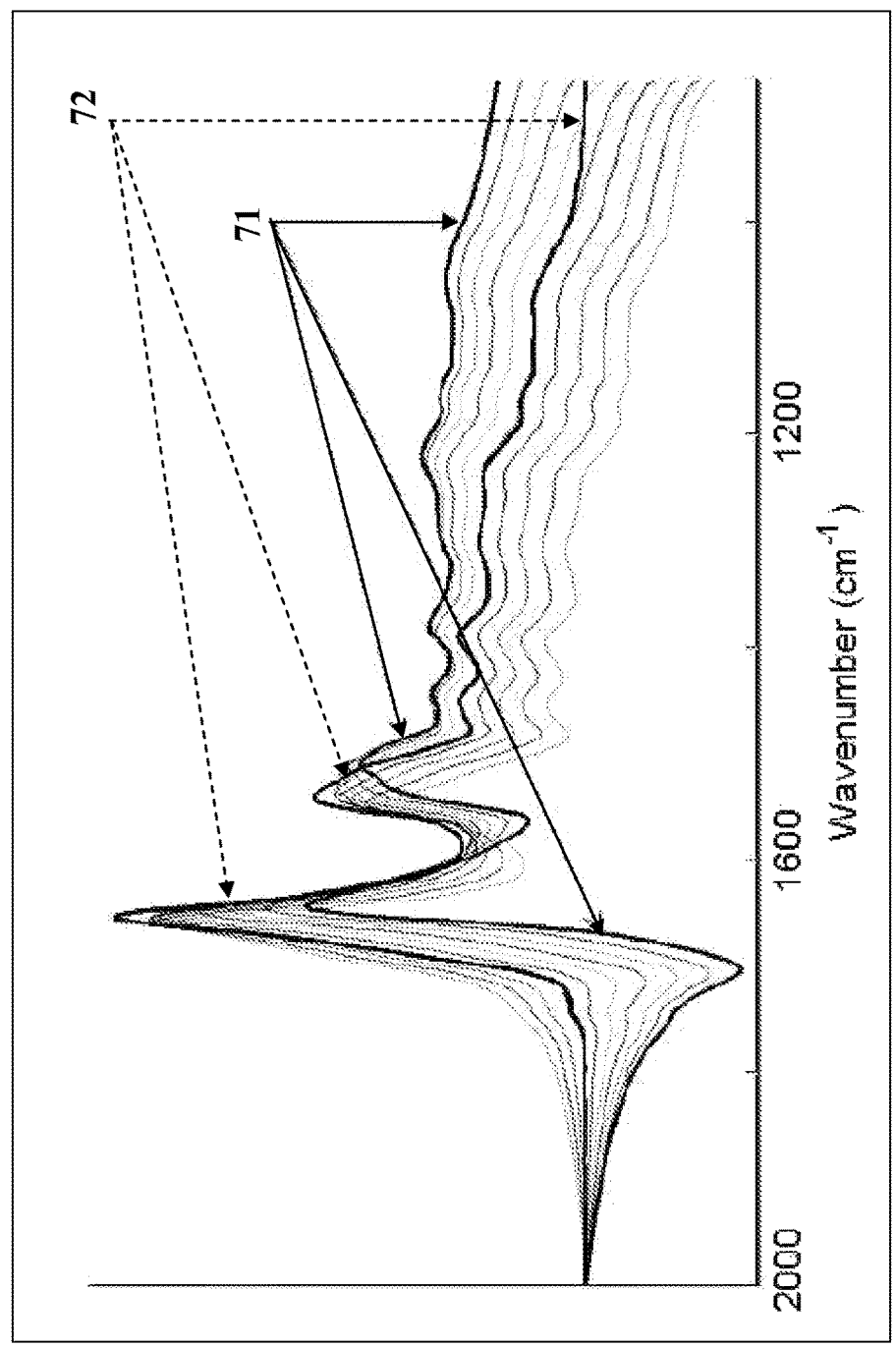
FIG. 7 is a series of traces depicting how an absorbance spectrum band shape contaminated by RMie scattering artifacts may be altered by varying the phase angle.

In step 18 of the embodiment of FIG. 1, the real (RE) and imaginary (IM) parts resulting from the Fourier analysis are subsequently "phase corrected" to yield phase shifted real (RE') and imaginary (IM') parts:

$$\begin{bmatrix} RE' \\ IM' \end{bmatrix} = \begin{bmatrix} \cos(\phi) & \sin(\phi) \\ -\sin(\phi) & \cos(\phi) \end{bmatrix} \begin{bmatrix} RE \\ IM \end{bmatrix}$$

where φ is the phase angle. The phase angle φ for the phase correction cannot be determined experimentally and varies spectrum to spectrum. Thus, in certain embodiments, the phase angle is determined using a stepwise approach between −90 and 90 degrees, or −π/2 and π/2, in user-defined increments (FIG. 1, step 18) until the optimal band shape of the recombined spectral parts is recognized (FIG. 1, decision 19). FIG. 7 demonstrates phase correction through a series of traces depicting an absorbance band shape contaminated by RMie scattering contributions 71 and how the band shape changes with various phase angles.

The optimal band shape is chosen based on peak position and intensity criteria, both of which vary during phase correction. As shown in FIG. 4, reflective contributions reduce the overall intensity of a spectral band shape. Thus, in most applications, the phase angle that produces the largest overall intensity after phase correction is likely to yield the optimal band shape. Because a second derivative spectrum exhibits reversal of the sign of spectral peaks, some embodiments may favor the phase angle that produces the largest negative intensity in the amide I band between 1650 and 1660 $cm^{-1}$. As seen in FIG. 7, the optimal band shape 72 not only produces the largest intensity after phase correction but also matches the peak position, at about 1655 $cm^{-1}$, of the uncontaminated spectrum.

In some embodiments, once the phase angle has been selected for an optimal band shape, the phase-shifted real and imaginary parts are recombined to yield a phase-corrected spectrum (FIG. 1, step 20).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

EXAMPLE

The following example demonstrates the operation of embodiments of the phase correction system and process.
Materials and Instrumentation
The emission device used in this example was a blackbody source operating at about 1300 kelvins (K) to emit a continuous infrared spectrum. The detection device was a photoconductive HgCdTe array operating at cryogenic temperatures. All computations were carried out using Intel-processor-based workstations, operating under Windows XP, Windows 7, or Linux.
Sample Characteristics
This example is based on a hyperspectral dataset collected from an excised human lymph node tissue section via SHP. The lymph node has confirmed breast cancer micro-metastases under the capsule. The photomicrograph in FIG. 9 shows distinct cellular nuclei in the cancerous region 91 as well as high cellularity in areas of activated lymphocytes 92. Both of these sample heterogeneities contribute to large RMie scattering effects, albeit at different wavenumbers.

A digital image of the lymph node section (FIG. 10) was obtained following data segmentation by hierarchical cluster analysis. Ten clusters were necessary to distinguish the cancerous tissue from the lymphocytes and the capsule, which was composed of more than one spectral class, together combined into one cluster. Overall, the distinction of these tissue types was poor.

Figure 11:
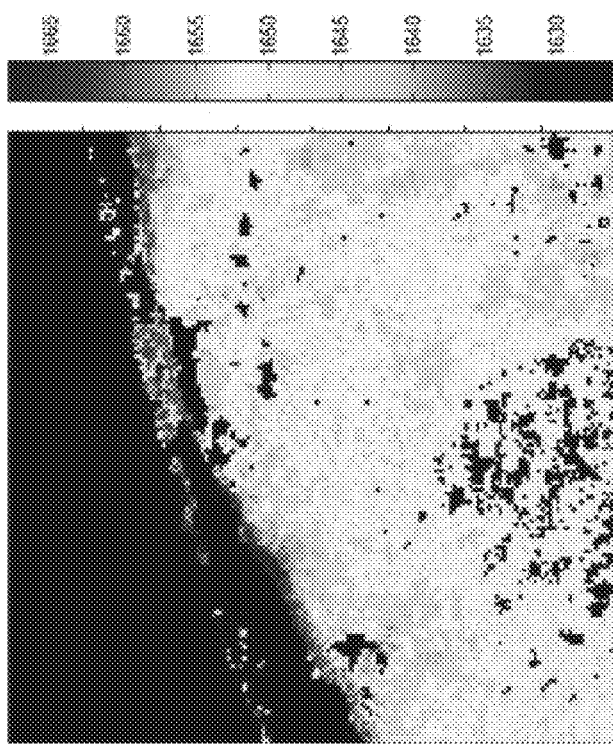
FIG. 11 is an image depicting the peak frequencies of the amide I vibrational band for a hyperspectral dataset contaminated by RMie scattering artifacts.

The difficulties in segmenting this hyperspectral dataset can be gauged by inspection of FIG. 11. This plot depicts the peak frequencies of the amide I vibrational band in each spectrum. The scale at right indicates that the peak occurred between about 1630 $cm^{-1}$ and 1665 $cm^{-1}$ for the lymph node body, and between $1635^{-1}$ and 1665 $cm^{-1}$ for the capsule. It is well-known that the amide I frequency for peptides and proteins should occur in the range from 1650 $cm^{-1}$ to 1660 $cm^{-1}$, depending on the secondary protein structure. Thus, the spread of amide I frequency was typical for a hyperspectral dataset heavily contaminated by RMie scattering effects.

Figure 12:
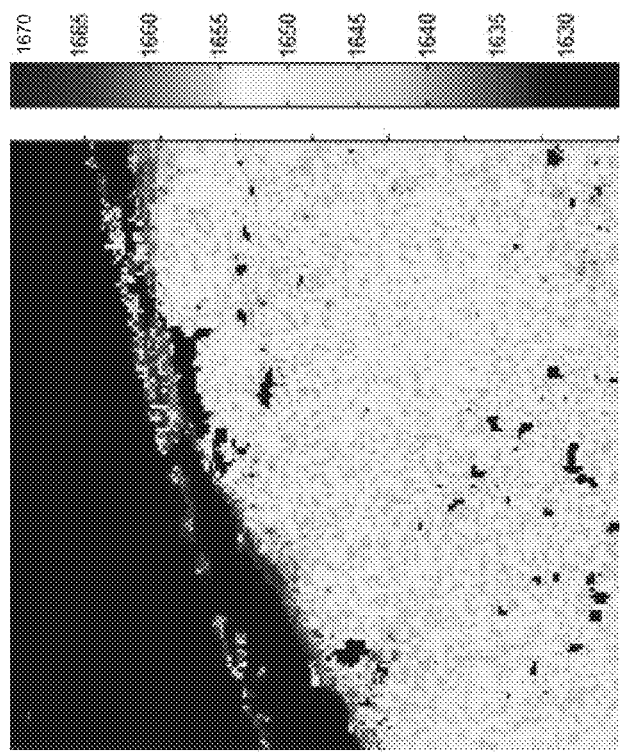
FIG. 12 is an image depicting the peak frequencies of the amide I vibrational band for a hyperspectral dataset following phase correction.
Figures 13, 14:
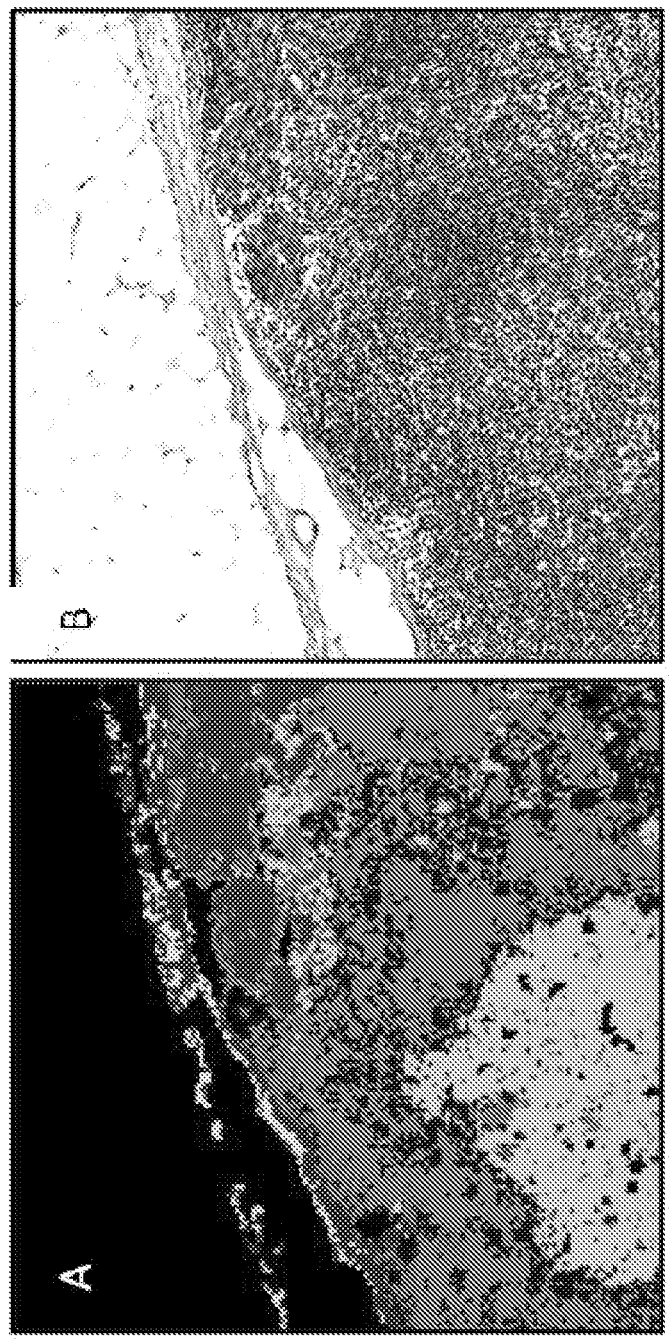
FIG. 13 is an image depicting a human lymph node tissue section obtained via hierarchical cluster analysis of a hyperspectral dataset following phase correction.
FIG. 14 is a photomicrograph of a human lymph node tissue section.

The individual spectra of the hyperspectral dataset were pre-processed by computing the second derivative of the signal intensity with respect to wavenumber, which was calculated using a Savitsky-Golay 11-point smoothing window to eliminate Mie scattering artifacts. The resulting second derivative spectra were each vector normalized and truncated to 512 data points in the infrared fingerprint region (778 to 1800 $cm^{-1}$), before undergoing reverse Fourier transform using a MATLAB-based FFT routine. After zero-filling the latter 256 data points of each resulting interferogram, forward Fourier transform using the MATLAB-based FFT routine resulted in a real part and an imaginary part of each spectrum in the dataset. The real and imaginary parts were recombined using phase angles varied in user-defined increments until the optimal absorbance band shape (i.e., the band shape with the largest overall intensity and correct peak position) was determined for each spectrum. Then, a second digital image comprising the corrected spectra was generated (FIG. 13, following further processing).
Results
Following the application of the embodied process, the distinction between tissue types of the lymph node section improved. FIG. 12 shows the peak frequencies of the amide I vibrational band in each spectrum after phase-correction of the RMie scattering distortions. The frequency variation of the amide I peak was reduced to a range of 1650 $cm^{-1}$ to 1654 $cm^{-1}$ for the lymph node body, and 1657 $cm^{-1}$ to 1665 $cm^{-1}$ for the capsule (fibro-connective proteins of the capsule are known to consist mostly of collagen, a protein known to exhibit a high amide I band position).

The results from the ensuing data segmentation by hierarchical cluster analysis are shown in FIG. 13. Unlike FIG. 10, the cancerous tissues, capsule tissues, activated B-lymphocytes, and T-lymphocytes are clearly distinguished from each other. Further comparison to the hematoxylin and eosin (H&E stain) histopathology photomicrograph of FIG. 14 indicates that the spectral analysis matches a visual examination nearly perfectly. Thus, the phase correction process greatly improved the quality of the spectral histopathology processes.

REFERENCES

[1] P. Wong, Wong, R., Caputo, T., Godwin, T., Rigas, B., *Proc. Natl. Acad. Sci.* 1991, 88, 10988.

[2] a) B. Bird, M. J. Romeo, M. Diem, K. Bedrossian, N. Laver, S. Naber, *Vibr. Spectrosc.* 2008, 48, 101; b) M. Romeo, Mohlenhoff, B., Jennings, M., Diem, M., *Biochim Biophys Acta* 2006, 1758, 915.

[3] a) K. Papamarkakis, B. Bird, J. M. Schubert, M. Miljković, R. Wein, K. Bedrossian, N. Laver, M. Diem, *Laboratory Investigations* 2010, 90, 589; b) J. M. Schubert, B. Bird, K. Papamarkakis, M. Miljković, K. Bedrossian, N. Laver, M. Diem, *Laboratory Investigations* 2010, 90, 1068.

[4] M. Diem, L. Chiriboga, H. Yee, *Biopolymers* 2000, 57, 282.

[5] a) M. J. Romeo, M. Diem, *Vibrational Spectrosc.* 2005, 38, 115; b) M. Romeo, S. Boydston-White, C. Matthaeus, M. Miljković, B. Bird, T. Chernenko, M. Diem, *Vibrational Microspectroscopy of Cells and Tissues*, Wiley-Interscience, Hoboken, N.J., 2008.

[6] P. Lasch, M. Diem, W. Hänsch, D. Naumann, *J. Chemometrics* 2007, 20, 209.

[7] a) B. Bird, K. Bedrossian, N. Laver, M. Miljkovic, M. J. Romeo, M. Diem, *The Analyst* 2009, 134, 1067; b) B. Bird, M. Romeo, M. Miljković, J. Smith, N. Stone, M. W. George, M. Diem, *BMC J. Clin. Pathology* 2008, 8, 1; c) B. Bird, M. Miljkovic, N. Laver, M. Diem, *Tech. Cancer Res. Treatment* 2011, 10, 135.

[8] M. Romeo, M. Diem, *Vibrational Spectroscopy* 2005, 38, 129.

[9] a) B. Mohlenhoff, Romeo, M. J., Diem, M., Wood, B. R., *Biophys J* 2005, 88, 3635; b) M. J. Romeo, B. Mohlenhoff, M. Diem, *Vibrational Spectrosc.* 2006, 42, 9.

[10] a) P. Bassan, H. J. Byrne, F. Bonnier, J. Lee, P. Dumas, P. Gardner, *Analyst* 2009, 134, 1586; b) P. Bassan, H. J. Byrne, J. Lee, F. Bonnier, C. Clarke, P. Dumas, E. Gazi, M. D. Brown, N. W. Clarke, P. Gardner, *Analyst* 2009, 134, 1171.

[11] P. Bassan, A. Kohler, H. Martens, J. Lee, H. J. Byrne, P. Dumas, E. Gazi, M. Brown, N. Clarke, P. Gardner, *Analyst* 2010, 135, 268.

[12] B. Bird, M. Miljković, M. Diem, *J. Biophoton.* 2010, 3 597.

[13] a) A. Kohler, C. Kirschner, A. Oust, H. Martens, *Appl. Spectrosc.* 2005, 59, 707; b) A. Kohler, J. Sule-Sosa, G. D. Sockalingum, M. Tobin, F. Bahramil, Y. Yang, J. Pijanka, P. Dumas, M. Cotte, D. G. van Pittius, G. Parkes, H. Martens, *Appl. Spectrosc.*, 2008, 62, 259.

[14] H. C. Van De Hulst, *Light Scattering by Small Particles*, Dover, Mineola, N.Y., 1981.

The invention claimed is:

1. A process of compensating for reflective distortions of optical spectra, the process comprising:
    scanning a sample with an energy emission to obtain at least one spectrum;
    performing a reverse Fourier transformation to obtain a real interferogram and an imaginary interferogram from the at least one spectrum;
    zero-filling the real and the imaginary interferograms;
    performing a forward Fourier transformation of the zero-filled real and the imaginary interferograms to obtain a real part and an imaginary part of the at least one spectrum; and
    recombining the real part and the imaginary part of the at least one spectrum using trial phase angles to obtain at least one corrected spectrum, the at least one corrected spectrum being substantially free of dispersive band shapes, and wherein the reflective distortions from a defined endpoint are corrected in the at least one corrected spectrum.

2. The process of claim 1, wherein the at least one spectrum comprises a multi-spectral or hyperspectral image.

3. The process of claim 1, wherein the at least one corrected spectrum comprises a corrected multi-spectral or hyperspectral image, the corrected multi-spectral or hyperspectral image being substantially free of dispersive effects.

4. The process of claim 1, performing the reverse Fourier transformation to obtain the real interferogram and the imaginary interferogram from the at least one spectrum comprises pre-processing the at least one spectrum.

5. The process of claim 4, wherein pre-processing the at least one spectrum comprises selecting a spectral range of the at least one spectrum.

6. The process of claim 5, wherein the spectral range is between 778 and 1800 $cm^1$.

7. The process of claim 4, wherein pre-processing the at least one spectrum comprises computing a second derivative of the at least one spectrum.

8. The process of claim 4, wherein pre-processing the at least one spectrum comprises vector normalizing the at least one spectrum.

9. The process of claim 4, wherein pre-processing the at least one spectrum comprises interpolating or truncating the at least one spectrum.

10. The process of claim 9, wherein the at least one spectrum is interpolated or truncated to a data point length which is an integer power of two.

11. The process of claim 1, wherein performing the reverse Fourier transformation comprises a Fast Fourier Transform algorithm.

12. The process of claim 1, wherein performing the forward Fourier transformation comprises a Fast Fourier Transform algorithm.

13. The process of claim 1, wherein zero-filling the real and the imaginary interferograms comprises adding zero-values to the end of each interferogram.

14. The process of claim 13, wherein a zero-filling factor is two.

15. The process of claim 1, wherein recombining the real part and the imaginary part of the at least one spectrum using trial phase angles to obtain at least one corrected spectrum comprises varying a phase angle between $-\pi/2$ and $\pi/2$ radians.

16. The process of claim 1, wherein recombining the real part and the imaginary part of the at least one spectrum using trial phase angles to obtain at least one corrected spectrum comprises varying a phase angle in user-defined increments.

17. A system for compensating for reflective distortions of optical spectra comprising a processor and a memory in electronic communication with the processor, wherein the memory stores computer executable code that when executed by the processor causes the processor to:
    scan a sample with an energy emission to obtain at least one spectrum;
    perform a reverse Fourier transformation to obtain a real interferogram and an imaginary interferogram from the at least one spectrum;
    zero-fill the real and the imaginary interferograms;
    perform a forward Fourier transformation of the zero-filled real and the imaginary interferograms to obtain a real part and an imaginary part of the at least one spectrum; and
    recombine the real part and the imaginary part of the at least one spectrum using trial phase angles to obtain at least one corrected spectrum, the at least one corrected spectrum being substantially free of dispersive band shapes, and wherein the reflective distortions from a defined endpoint are corrected in the at least one corrected spectrum.

18. The system of claim 17, wherein executable code being stored on one or more memory devices.

19. The system of claim 17, further comprising executable code that when executed by the processor cause the processor to pre-process the at least one spectrum.

20. The system of claim 17, further comprising executable code that when executed by the processor cause the processor to select a spectral range of the at least one spectrum.

21. The system of claim 17, further comprising executable code that when executed by the processor cause the processor to compute a second derivative of the at least one spectrum.

22. The system of claim 17, further comprising executable code that when executed by the processor cause the processor to interpolate the at least one spectrum.

23. The system of claim 22, wherein the at least one spectrum is interpolated or truncated to a data point length which is an integer power of two.

24. The system of claim 17, further comprising executable code that when executed by the processor cause the processor to perform a Fast Fourier Transform algorithm.

25. The system of claim 17, further comprising executable code that when executed by the processor cause the processor to add zero-values to the end of each interferogram.

26. The system of claim 25, wherein a zero-filling factor is two.

27. The system of claim 17, further comprising executable code that when executed by the processor cause the processor to vary a phase angle between $\pi/2$ and $\pi/2$ radians.

28. The system of claim 17, further comprising executable code that when executed by the processor cause the processor to vary a phase angle in user-defined increments.

29. The system of claim 17, further comprising at least one energy emission device for generating a waveform.

30. The system of claim 17, further comprising at least one detection device for obtaining at least one spectrum from a sample.

31. A process of correcting optical spectra for distortions resulting from anomalous dispersion of the refractive index, the process comprising:
   scanning a sample with an energy emission to obtain at least one spectrum;
   performing a reverse Fourier transformation to obtain a real interferogram and an imaginary interferogram from the at least one spectrum;
   zero-filling the real and the imaginary interferograms;
   performing a forward Fourier transformation of the zero-filled real and the imaginary interferograms to obtain a real part and an imaginary part of the at least one spectrum; and
   recombining the real part and the imaginary part of the at least one spectrum using trial phase angles to obtain at least one corrected spectrum, the at least one corrected spectrum being substantially free of dispersive band shapes, and wherein the reflective distortions from a defined endpoint are corrected in the at least one corrected spectrum.

32. The process of claim 31, wherein the distortions are not caused by interaction of reflectance and absorbance.

33. The process of claim 31, wherein the distortions are caused in Coherent Anti-Stokes Raman Spectroscopy (CARS).

34. A system for compensation of optical spectra where distortions are caused by non-resonant and resonant signal components, the system comprising a processor and a memory in electronic communication with the processor; wherein the memory stores computer executable code that when executed by the processor cause the processor to:
   scan a sample with an energy emission to obtain at least one spectrum;
   perform a reverse Fourier transformation to obtain a real interferogram and an imaginary interferogram from the at least one spectrum;
   zero-fill the real and the imaginary interferograms;
   perform a forward Fourier transformation of the zero-filled real and the imaginary interferograms to obtain a real part and an imaginary part of the at least one spectrum; and
   recombine the real part and the imaginary part of the at least one spectrum using trial phase angles to obtain at least one corrected spectrum, the at least one corrected spectrum being substantially free of dispersive band shapes, and wherein the reflective distortions from a defined endpoint are corrected in the at least one corrected spectrum.

35. The system of claim 34, wherein the distortions are not caused by interaction of reflectance and absorbance.

36. The system of claim 34, wherein the distortions are caused in Coherent Anti-Stokes Raman Spectroscopy (CARS).

* * * * *